United States Patent
Buchbinder et al.

(10) Patent No.: US 8,884,056 B2
(45) Date of Patent: Nov. 11, 2014

(54) ANAEROBIC CONVERSION OF 4-CARBOXYBENZALDEHYDE IN IONIC LIQUIDS

(71) Applicant: UOP LLC, Des Plaines, IL (US)

(72) Inventors: Avram M. Buchbinder, Chicago, IL (US); Alakananda Bhattacharyya, Glen Ellyn, IL (US); Joel T. Walenga, Lake Zurich, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/715,571

(22) Filed: Dec. 14, 2012

(65) Prior Publication Data

US 2014/0171680 A1     Jun. 19, 2014

(51) Int. Cl.
*C07C 51/487*     (2006.01)

(52) U.S. Cl.
CPC .................................. *C07C 51/487* (2013.01)
USPC ....................................................... 562/473

(58) Field of Classification Search
None
See application file for complete search history.

(56) References Cited

U.S. PATENT DOCUMENTS

| | | | |
|---|---|---|---|
| 6,207,872 B1 | 3/2001 | Barger et al. | |
| 7,071,136 B2 | 7/2006 | Chang et al. | |
| 7,329,625 B2 | 2/2008 | Chang | |
| 7,547,812 B2 | 6/2009 | Sinkler et al. | |
| 7,578,987 B2 | 8/2009 | Wilson | |
| 7,772,337 B2 | 8/2010 | Chang et al. | |
| 7,922,997 B2 | 4/2011 | Moscoso et al. | |
| 7,947,621 B2 | 5/2011 | Chang et al. | |
| 7,973,208 B2 | 7/2011 | Sinkler et al. | |
| 2003/0129128 A1 | 7/2003 | Strohmaier et al. | |
| 2005/0054516 A1 | 3/2005 | Vaughn et al. | |
| 2007/0010688 A1* | 1/2007 | Ko et al. | 562/533 |
| 2010/0174111 A1* | 7/2010 | Rogers et al. | 562/486 |
| 2012/0004456 A1* | 1/2012 | Bhattacharyya | 562/485 |

FOREIGN PATENT DOCUMENTS

| | | |
|---|---|---|
| EP | 2 098 287 A1 | 9/2009 |
| WO | WO 2005/056184 | 6/2005 |

OTHER PUBLICATIONS

Kang et al. Journal of Industrial and Engineering Chemistry 2012, 174-177.*

Weyda et al., "Kinetic Studies of the Crystallination of Aluminophosphate . . . " Studies in Surface Science and Catalysis, vol. 49, Issue C, 1989, pp. 169-178.

Schreyeck et al., "The diaza-polyoxa-macrocycle 'Kryptofix222' as a new . . . ," Microporous and Mesoporous Materials 22, (1998) pp. 87-106.

Fayad et al., "A Rational Approach to the Ionothermal Synthesis of an . . . ," Angew. Chem. Int. Ed. 2010, 49, pp. 4585-4588.

* cited by examiner

*Primary Examiner* — Brandon Fetterolf
*Assistant Examiner* — Ana Z Muresan
(74) *Attorney, Agent, or Firm* — Mark R Willis

(57) ABSTRACT

A method of decreasing an amount of an aromatic aldehyde in a product is described. The method includes reacting the aromatic aldehyde in the presence of a reaction medium comprising a nucleophilic solvent, or an ionic liquid and a carboxylic acid, the reaction taking place in the absence of a hydrogenating agent and an oxidizing agent, to form aromatic carboxylic acid, an aromatic alcohol, or both.

20 Claims, No Drawings

ANAEROBIC CONVERSION OF 4-CARBOXYBENZALDEHYDE IN IONIC LIQUIDS

FIELD OF THE INVENTION

This invention relates to processes for decreasing the amount of aromatic aldehyde impurities by converting the aromatic aldehyde to another product or products. More particularly, the invention relates to processes for reducing the level of aromatic aldehyde impurities in an aromatic carboxylic acid product using ionic liquids.

BACKGROUND OF THE INVENTION

Oxidation of alkyl aromatic compounds, e.g., toluene and xylenes are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing an alkyl-aromatic compound. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Bronstead acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. No. 7,692,036, US 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

US 2012/0004449, 2012/0004450, 2012/0004454, each of which is incorporated herein by reference describe processes and mixtures for oxidizing alkyl aromatic compounds, such as terephthalic acid. The process involves forming a mixture comprising the alkyl-aromatic compound, a solvent, a bromine source, and a catalyst, and contacting the mixture with an oxidizing agent at oxidizing conditions to produce an oxidation product comprising at least one of an aromatic aldehyde, and aromatic alcohol, an aromatic ketone, and an aromatic carboxylic acid. The solvent comprises a carboxylic acid having one to seven carbon atoms and an ionic liquid selected from an imidazolium ionic liquid, a pyridinium ionic liquid, a phosphonium ionic liquid, a tetra alkyl ammonium ionic liquid, or combinations thereof.

US 2012/0004456, which is incorporated herein by reference, describes a process for purifying crude terephthalic acid with a solvent comprising an ionic liquid at purifying conditions to produce a solid terephthalic acid product having a concentration of contaminant lower than the first concentration.

SUMMARY OF THE INVENTION

One aspect of the invention is a method of decreasing an amount of an aromatic aldehyde. In one embodiment, the method includes reacting the aromatic aldehyde in the presence of a reaction medium comprising a nucleophilic solvent, or an ionic liquid and a carboxylic acid, the reaction taking place in the absence of a hydrogenating agent and an oxidizing agent, to form an aromatic carboxylic acid, an aromatic alcohol, or both.

DETAILED DESCRIPTION OF THE INVENTION

This invention involves a process for reacting aromatic aldehydes, such as 4-CBA, to form the desired aromatic carboxylic acid product, such as terephthalic acid, and an aromatic alcohol product, such as 4-hydroxymethylbenzoic acid (4-HMBA), that is more soluble than the aromatic carboxylic acid product in the chosen reaction medium. The reaction takes place in the presence of an inert gas and in the absence of either a hydrogenating agent, or an oxidizing agent. Suitable inert gases include, but are not limited to nitrogen, helium, argon, and other noble gases. Typically, no catalyst is included. The process can be used as part of a process for making aromatic carboxylic acids, as well as for purifying aromatic carboxylic acids made using other processes.

The invention utilizes a reaction medium comprising a nucleophilic solvent, or an ionic liquid solvent, and optionally a carboxylic acid. The reaction is conducted at high temperature and pressure. It results in conversion of the aromatic aldehyde, such as 4-CBA, to an aromatic alcohol, such as 4-HMBA, and/or an aromatic carboxylic acid, such as terephthalic acid, rather than hydrogenation to 4-HMBA, toluic acid, and other hydrogenation products.

The starting material to be converted comprises an aromatic aldehyde, such as 4-CBA. The starting material can optionally comprise an aromatic carboxylic acid or dicarboxylic acid, such as terephthalic acid or toluic acid. The aromatic aldehyde comprises between 50 ppm wt and 100 wt % of the starting material, or between 1 wt % and 100 wt % of the starting material, or between 5 wt % and 50 wt %.

The total amount of starting material can comprise about 0.1 wt % to about 50 wt % of the total reaction medium, or about 0.1 wt % to about 40 wt % of the total reaction medium, or about 0.1 wt % to about 30 wt % of the total reaction medium, or about 0.1 wt % to about 20 wt % of the total reaction medium, or about 1% to about 10 wt % of the total reaction medium.

For this reaction, the important factor for the composition and concentration of the starting material appears to be the amount of aromatic aldehyde in the total reaction medium. Thus, the higher the amount of aromatic aldehyde in the starting material, the lower the amount of starting material in the total reaction medium would need to be to obtain the same amount of aromatic aldehyde in the total reaction medium.

Although the following discussion focuses on 4-CBA as the aromatic aldehyde, terephthalic acid as the aromatic carboxylic acid, and 4-HMBA as the aromatic alcohol, those of skill in the art will understand that other aromatic aldehydes can be used to form other aromatic carboxylic acids, and aromatic alcohols. For example, benzaldehyde can be converted to benzoic acid and benzyl alcohol, 3-CBA can be converted to isophthalic acid and 3-HMBA, and 2-CBA can be converted to phthalic acid, (which can further react to form phthalic anhydride), and 2-HMBA.

It should be noted that, as used herein, the terms aromatic alcohol, aromatic aldehyde, and aromatic carboxylic acid do not limit additional substituent functional groups of the molecules involved. For instance, the aromatic aldehyde, such as 4-CBA, may contain both an aldehyde group and a carboxylic acid substituent, and the aromatic carboxylic acid, such as terephthalic acid, may contain one carboxylic acid substituent, or two or more carboxylic acid substituents. Also, the term carboxylic acid encompasses both carboxylic acids and their conjugate bases, also known as carboxylates.

The reaction of the aromatic aldehyde can be combined with separation methods known in the art, such as washing, solvent contacting, and/or filtering steps in order to remove ionic liquid and carboxylic acid, other solvent, and the soluble aromatic alcohol impurity from the purified aromatic carboxylic acid product.

There are many ways to accomplish separation of the components. For instance, if the aromatic carboxylic acid is terephthalic acid, it can be separated by crystallization by decreasing temperature or adding an anti-solvent, followed by filtration and washing. The liquid that remains from the filtration step, known as a mother liquor, contains soluble 4-HMBA, ionic liquid, carboxylic acid, other solvent components, and any remaining 4-CBA. The mother liquor can be re-used as the solvent for purifying an additional batch of feed containing aromatic aldehyde, recycled for the same purpose in a continuous process, or used as a solvent for a different type of reaction such as oxidation of alkyl aromatic compounds (as in US 2012/0004450 or US 2012/0004449) or purification of CTA by oxidation (as in US 2012/0004456).

If isolation of the soluble 4-HMBA is desired, it can be separated from the remaining liquid using extraction, crystallization by addition of an anti-solvent or cooling, chromatography, removal of the solvent by evaporation or other means, or other separation methods known in the art. If the solvent is going to be re-used or recycled and 4-HMBA and 4-CBA remaining in solution is undesirable, they can be isolated using extraction, crystallization, chromatography or other separation methods known in the art, or they can be transformed to terephthalic acid by oxidation according to methods known in the art (as in US2012/0004450 or US 2012/0004449), followed by crystallization and filtration.

Although not wishing to be bound by theory, the observed conversion of 4-CBA to 4-HMBA and terephthalic acid could be due to a disproportionation reaction, which would follow a second order reaction rate law in the concentration of 4-CBA.

Alternatively, 4-HMBA could be generated from a reaction of 4-CBA with a nucleophile followed by elimination of water, and terephthalic acid could be formed by reaction with a nucleophile followed by hydrogen atom abstraction.

Another alternative is that some free radical oxidants may be produced due to the presence of bromide ions and acetic acid which could react to form hydrogen bromide. As is well known, hydrogen bromide is a source for Br radicals which can abstract a hydrogen atom from 4-CBA followed by addition of an OH radical to form terephthalic acid.

The product contains less 4-CBA than the starting material. For example, the product typically contains less than about 60% of the original amount of 4-CBA, or less than about 50% of the original amount of 4-CBA, or less than about 40% of the original amount of 4-CBA, or less than about 30% of the original amount of 4-CBA, or less than about 20% of the original amount of 4-CBA, or less than about 10% of the original amount of 4-CBA, or less than about 5% of the original amount of 4-CBA, or less than 1% of the original amount of 4-CBA. Desirably, the product contains less than about 2500 ppm 4-CBA or less than about 1000 ppm 4-CBA or less than about 750 ppm 4-CBA or less than about 500 ppm 4-CBA or less than about 250 ppm 4-CBA or less than about 100 ppm 4-CBA or less than about 50 ppm 4-CBA, or less than about 25 ppm 4-CBA.

The reacting step(s) may be practiced in laboratory scale experiments through full scale commercial operations. The process may be operated in batch, continuous, or semi-continuous mode. The contacting step can take place in various ways. The order of addition of the components (e.g., aromatic aldehyde, solvent) is not critical. For example, the components can be added individually, or two or more components may be combined or mixed before being combined or mixed with other components.

The solvent comprises one or more of nucleophilic solvents, ionic liquids, and optionally carboxylic acids. In some embodiments, the reaction medium comprises a nucleophilic solvent. Suitable nucleophilic solvents include, but are not limited to, water, alcohols, ethers, amides such as amides, acetamide, nitriles, ketones, ammonia, amines, pyridine or combinations thereof. In some embodiments, the reaction medium comprises one or more ionic liquids.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Cations and anions for ionic liquids are described in US Publication 2010/0174111, for example.

The organic cation can comprise a linear, branched, or cyclic heteroalkyl unit. The term "heteroalkyl" refers to a cation comprising one or more heteroatoms chosen from nitrogen, oxygen, sulfur, boron, arsenic, boron, antimony, aluminum, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The anionic portion of the ionic liquid can comprise an inorganic, organic, or organometallic moiety. Non-limiting examples of anions include inorganic anions: halogens, (e.g., F, Cl, Br, and I); borides, $BX_4$, wherein X represents halogen, (e.g., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; $CO_3^{2-}$; $NO_2^{1-}$, $NO_3^{1-}$, $SO_4^{2-}$, $PO_4^{3-}$, $(CF_3)SO_3^{1-}$.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R)_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In some embodiments, ionic liquids suitable for use include, but are not limited to, one or more of imidazolium ionic liquids, pyridinium ionic liquids, phosphonium ionic liquids, tetra alkyl ammonium ionic liquids, pyrrolidinium ionic liquids, and pyrazolium ionic liquids, their alkyl derivatives, and combinations thereof. More than one ionic liquid may be used, if desired. Imidazolium, pyridinium, and ammonium ionic liquids have a cation comprising at least one nitrogen atom. Phosphonium ionic liquids have a cation comprising at least one phosphorus atom. In some embodiments, the ionic liquid comprises a cation selected from alkyl imidazolium, di-alkyl imidazolium, and combinations thereof. In some embodiments, the ionic liquid comprises an anion selected from halides, acetate, carboxylates, and combinations thereof. The ionic liquid may comprise at least one of 1-butyl 3-methyl imidazolium acetate (BMImOAc), 1-butyl 3-methyl imidazolium bromide (BMImBr), 1-hexyl 3-methyl imidazolium acetate, and 1-hexyl 3-methyl imidazolium bromide.

The ionic liquid can be provided, or it can be generated in situ from appropriate precursors, or both. If it is generated in situ, the reaction medium comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates. In an embodiment, the precursors are methyl imidazole and butyl bromide.

The mode of introducing the ionic liquid precursors may vary depending on the nature of the aromatic aldehydes being reacted and the nature and purity of the product desired. In one mode of addition, the cation precursors and the anion precursors (generally liquids at room temperature and pressure) are mixed with a carboxylic acid (for example, acetic acid) solvent and introduced into the reactor(s). In another mode of addition, the ionic liquid precursors may be mixed with the aromatic aldehyde feed and introduced into the reactors. In another mode of addition, both cation and anion ionic liquid precursor components may be introduced into the bottom of the reactor without pre-mixing with any other components such as the feed, and carboxylic acid.

The reaction medium can also comprise one or more carboxylic acids. When carboxylic acids are used in the reaction medium, the amount of carboxylic acid is decreased compared with conventional oxidation processes in order to avoid excessive solvent volumes. The carboxylic acid desirably has from 1 to 7 carbon atoms. In an embodiment, the carboxylic acid comprises acetic acid. In another embodiment, the reaction medium may further comprise benzoic acid.

Optionally, the reaction medium can include one or more bases comprising nitrogen, such as one or more of ammonia, a dialkylammonium compound, a trialkylammonium compound, pyridine, pyridine derivatives such as collidine, an amide such as acetamide, or one or more of the salts of the conjugate acids of one or more bases comprising nitrogen which can include ammonium acetate, ammonium hydroxide, trialkylammonium acetate, dialkylammonium acetate, dialkylammonium hydroxide, and combinations thereof. The amount of these compounds ranges from about 0.1 wt % to about 50 wt %, relative to the total weight of the mixture not including the reactant, or from about 15 wt % to about 25 wt %. The resulting pH of the medium, if a carboxylic acid is included, ranges from about 1 to about 5. Alternatively, the pH ranges from about 1 to about 10. If a carboxylic acid is not included the pH ranges from about 3 to about 14.

Optionally, the reaction medium may further comprise water as or in addition to the nucleophilic solvent. The water may be added to the mixture or generated in the mixture during the process. In an embodiment, the amount of water ranges from about 0.01 wt % to about 10 wt %, relative to the total weight of the mixture not including the reactant, or from about 4 wt % to about 6 wt %, relative to the total weight of the mixture not including the reactant. The amount of water added to the mixture is typically in the range of about 0.01 wt % to about 5 wt %. Additional water can be formed by reaction of some components, such as ammonium acetate reacting to form acetamide and water.

Bromine sources can be included, but are not required. Suitable bromine sources include bromine, ionic bromine, e.g. HBr, NaBr, KBr, $NH_4Br$, or ionic bromine that is a component of an ionic liquid; and/or organic bromides which are known to provide bromide ions at the reaction conditions, such as, benzylbromide, mono and di-bromoacetic acid, bromoacetyl bromide, tetrabromoethane, ethylene di-bromide. The amount of bromine (i.e., not the amount of bromine salt or other bromine compound) may range from about 0.05 wt % of bromine content to about 8.5 wt % of bromine content relative to the total weight of the mixture not including the reactant.

At least a portion of the components provides a liquid phase, although dissolution of one or more of the mixture components may not be complete at any or some time during the process. The liquid phase may be formed by mixing the components at ambient conditions. In another embodiment, the liquid phase is formed as the temperature of the mixture increases to the reaction temperature. A mixture of the components may be formed prior to the reaction step, in the same or different vessel as that used in the reaction step. In another embodiment, a mixture of the components is formed in a reactor, e.g. adding various streams of the components individually and/or in combination to a continuous or semi-continuous reactor. The combined components, and/or various streams of the components may be heated before they are mixed together.

Though many conventional conversions of alkyl aromatics and their derivatives such as alkyl aromatic oxidation processes are typically conducted in a mixed phase, and often include three phases (e.g. solid, gas, and liquid), they are frequently referred to in the art as "liquid phase" processes because the conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase reactors as known in the art may be used to practice the invention. Examples include vessels, which may have one or more mechanical agitators, and various bubble column reactors such as those described in U.S. Pat. No. 7,692,036. It is also known to design, operate, and control such reactors and the reaction for the conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The reacting step[s] can take place at a temperature ranging from about 200° C. to about 275° C. and a pressure ranging from about atmospheric, i.e., 0 MPa(g), to about 6 MPa(g) and a residence time ranging from about 30 seconds to about 2 weeks. That is, the mixture has a temperature and a pressure within these ranges and may be maintained within these ranges for a period of time within the residence time range. The temperature, pressure and residence time may vary based on a variety of factors including for example, the reactor configuration, size, and whether the process is, batch, continuous, or semi-continuous. One condition may also vary based on other conditions. For example, use of a particular temperature range may enable use of a different residence time range.

In one embodiment, the reaction medium includes acetic acid, an imidazolium based ionic liquid, ammonium acetate, and water. In this embodiment, the reaction was performed at about 2.8 MPa (400 psig) of an inert gas ($N_2$) at about 200° C. for 2 hours. In another embodiment, the reaction was performed instead at about 216° C. for 2 hours.

In an embodiment, the terephthalic acid produced by the instant invention may precipitate, crystallize, or solidify in a liquid phase mixture at the reaction conditions and/or as the mixture cools. The terephthalic acid can be recovered from the solution using one of more of separation, filtering, washing, drying, and solvent extraction, for example. It can be further purified as discussed below.

In another embodiment, the reaction results in a concentration of terephthalic acid below the solution saturation concentration. In such embodiments, terephthalic acid remains dissolved in the liquid phase at room temperature, and could be separated by cooling below room temperature resulting in crystallization, or by adding an anti-solvent such as additional water or additional acetic acid. Alternatively, the dissolved terephthalic acid could be isolated by distillation of the solvent to increase the concentration of terephthalic acid and cause crystallization, or by chromatographic methods or other methods known in the art for separating dissolved solids from a liquid medium.

The soluble 4-HMBA can be separated from the crystallized terephthalic acid and the rest of the reaction mixture. If isolation of the soluble 4-HMBA is desired, it can be separated from the remaining liquid using extraction, crystallization by addition of an anti-solvent or cooling, chromatography, or other separation methods known in the art. If the solvent is going to be re-used or recycled, and having 4-HMBA and 4-CBA remain in solution is undesirable, they can be isolated using extraction, crystallization, chromatography or other separation methods known in the art After isolation, or as a solution in the reaction solvent or other solvent, 4-HMBA could be utilized, for example, as an additive to a polymer or resin, or used as the starting material to derivatize by further reactions. Such reactions could be used, in some non-limiting examples, to produce a chloro- bromo- or iodomethylbenzoic acid, a hydroxymethylbenzoate ester, a hydroxymethylbenzic acid halide, a hydroxymethylbenzoate amide, a mehtylbenzoic acid ether, a hydroxymethylbenzoate anhydride, or a hydroxymethylbenzoate salt.

The invention provides new ways to control the level of various contaminants in the product. The process may reduce costs because it requires less equipment and it does not require expensive metal catalyst.

In some embodiments, the invention further comprises purifying the aromatic carboxylic acid product. Purifying may comprise one or more additional steps to isolate and purify the product. Examples of purifying steps include: separating wherein the product is separated from the liquid phase such as by filtration and/or centrifugation; washing wherein the product is washed, for example with water and/or another solvent component; and drying the product. Separation of aromatic carboxylic acid product from the reaction mixture can also be accomplished by adding an anti-solvent such as additional water or additional carboxylic acid such as acetic acid. Such additional processing steps have been described in the general literature and are well known to those of ordinary skill in the art to be used in various combinations to purify products of the invention. See for example, the references cited in this application and the art cited therein.

A purification step of the instant invention may further comprise one or more solvent contacting steps. A solvent contacting step comprises contacting a product, also including washed or dried solid products, with another solvent comprising at least one of water, a carboxylic acid, an ionic liquid and/or ionic liquid precursor, and a mother liquor to produce a purified product. In an embodiment, the solvent of the solvent contacting step contains ionic liquid and carboxylic acid, and optionally mother liquor. The composition of the solvent for the solvent contacting step can be as described above for the reacting step.

Solvent contacting may leach impurities from the solid product, and/or the product may be partially or completely dissolved in the solvent. Solvent contacting conditions include a solvent contacting temperature. The solvent contacting temperature may be lower than the reaction temperature. In an embodiment, the solvent contacting temperature is at least 20° C. lower than the reaction temperature. Solvent contacting may be practiced, for example, in one or more crystallizers that follow the reactor. The product may solidify, precipitate, or crystallize in the solvent of the solvent contacting step.

It should be noted that the terms "first", "second", and "third" etc. are being used to distinguish one component, or composition, or stage, or zone, or reactor etc. from another. It is not necessarily the case that a "second" stage or zone, for example, physically or temporally follows a "first" stage or zone. Depending on the context, it could be before or after, as would be understood by those of skill in the art.

EXAMPLES

The examples are presented to further illustrate some aspects and benefits of the invention and are not to be considered as limiting the scope of the invention.

Example 1

The reaction medium was a blend comprising 47 wt % acetic acid, 9.5 wt % 1-butyl-3-methylimidazolium (BMIm) acetate, 19 wt % BMIm bromide, 19 wt % ammonium acetate, and 5 wt % water. To this blend, 4-CBA was added such that its weight percent was 9.7% on the basis of the resulting reaction medium including 4-CBA.

In one trial, the reaction medium was heated in a titanium vessel to 216° C. under a $N_2$ atmosphere and sampled through a dipleg covered with a 10 micron mesh titanium filter, into a titanium pressure vessel. Thus, only products contained in the liquid phase were sampled (the solid phase was rejected).

The temperature was cooled to 200° C., and the procedure was repeated.

After cooling to room temperature, the sample, which included both liquids and solids at room temperature, was diluted 200:1 in ammonium hydroxide, which resulted in complete dissolution of all solids. The sample was then analyzed by HPLC.

At 216° C. after 2 hr, the liquid phase was found to contain 6.06 mmol/100 g 4-HMBA, 5.60 mmol/100 g terephthalic acid, 0.84 mmol/100 g p-toluic acid, 28.17 mmol/100 g 4-CBA, and unidentified products. (The toluic acid may have been present as an impurity in the starting material.)

After an additional 2 hr at 200° C. and cooling to room temperature, the reaction products (liquid+solid) were analyzed and found to contain 7.68 mmol/100 g 4-HMBA, 5.70 mmol/100 g terephthalic acid and 22.73 mmol/100 g 4-CBA, 0.61 mmol/100 g p-toluic acid, in addition to other unidentified products. The total conversion of 4-CBA after the reaction was 64.9%.

Example 2

In another trial, the same experiment was conducted, but the filter on the sampling dipleg was omitted. This ensures that all reaction products, solid and liquid, were collected. Also, the mixture was heated to 204° C. first and then to 216° C. in order to determine if the reaction requires activation at the higher temperature.

The products of this reaction after 2 hr at 204° C. were 6.44 mmol/100 g 4-HMBA, 7.73 mmol/100 g terephthalic acid, 46.51 mmol/100 g 4-CBA, 0.94 mmol/100 g p-toluic acid, and unidentified products.

Subsequently, the reaction was heated to 216° C. for 2 hr, and the contents were 21.77 mmol/100 g 4-HMBA, 10.93 mmol/100 g terephthalic acid, 34.12 mmol/100 g 4-CBA and 0.77 mmol/100 g p-toluic acid, and unidentified products. The total conversion of 4-CBA after reaction and the subsequent cooling period was 57.5%.

Example 3

The reaction was repeated with a 4-CBA concentration of 1 wt %. Here, the total conversion after 2 hours at 204° C. and an additional 2 hours at 216° C. was 54%. The products of the reaction after 2 hr at 204° C. were 1.46 mmol/100 g terephthalic acid, and 6.02 mmol/100 g 4-CBA, and unidentified products. The products after 2 hr at 216° C. were 0.99 mmol/100 g terephthalic acid, and 4.04 mmol/100 g 4-CBA, and unidentified products.

No 4-HMBA was observed. Either 4-HMBA was not produced, or the small amount of 4-HMBA produced in the 1% reaction may be below the detection limit, or it may react to form other products. This implies that the reaction that took place in the 10% mixture may be a second order reaction in 4-CBA, such as a disproportionation reaction. Alternatively, the reaction may be at equilibrium (such as a nucleophilic substitution reaction), and it may require more 4-CBA in order to generate 4-HMBA.

Comparative Example 4

A similar reaction was attempted in a medium consisting of 82.4 wt % acetic acid and 8.24% water and 9.36 wt % 4-CBA. The reactor was heated to 204° C. for 2 hours, followed by 3 hours at 177° C. After cooling and analyzing, this reaction resulted in no products above 0.07 wt % other than unconverted 4-CBA in either the solid or liquid.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of decreasing the amount of an aromatic aldehyde in a composition comprising:
reacting the aromatic aldehyde in the presence of a reaction medium comprising a nucleophilic solvent, an ionic liquid, or combinations thereof, and a carboxylic acid, the reaction taking place at a pH in a range of 1 to 5 in the absence of a hydrogenating agent and an oxidizing agent, to form an aromatic carboxylic acid, an aromatic alcohol or both.

2. The method of claim 1 wherein the reaction medium comprises the nucleophilic solvent and wherein the nucleophilic solvent comprises water, alcohols, ethers, amides, nitriles, ketones, or combinations thereof.

3. The method of claim 1 wherein the reaction medium comprises the ionic liquid and wherein the ionic liquid comprises an imidazolium-based ionic liquid, a pyridinium-based ionic liquid, a phosphonium-based ionic liquid, a tetraalkylammonium-based ionic liquid, a pyrrolidinium-based ionic liquid, a pyrazolium-based ionic liquid, or combinations thereof.

4. The method of claim 1 wherein the carboxylic acid comprises acetic acid.

5. The method of claim 1 wherein the reaction medium further comprises ammonia, ammonium acetate, ammonium hydroxide, a dialkyl ammonium compound, pyridine, salts thereof, or combinations thereof.

6. The method of claim 1 wherein the reaction takes place at a temperature greater than 200° C.

7. The method of claim 1 further comprising recovering the aromatic carboxylic acid.

8. The method of claim 7 further comprising purifying the recovered aromatic carboxylic acid.

9. The method of claim 1 further comprising isolating the aromatic alcohol.

10. The method of claim 1 further comprising adding solid aromatic carboxylic acid containing solid aromatic aldehyde to the reaction medium before reacting the aromatic aldehyde.

11. The method of claim 1 further comprising introducing a solution containing the aromatic aldehyde, an aromatic carboxylic acid starting material, and a second solvent to the reaction medium before reacting the aromatic aldehyde.

12. The method of claim 11 wherein the second solvent comprises a carboxylic acid, an ionic liquid, or combinations thereof.

13. The method of claim 1 wherein the aromatic aldehyde is 4-carboxybenzaldehyde, and wherein the aromatic carboxylic acid is terephthalic acid, and the aromatic alcohol is 4-hydroxymethylbenzoic acid.

14. The method of claim 13 wherein the reaction medium contains more than 1% 4-carboxybenzaldehyde based on total reaction medium.

15. The method of claim 13 wherein the reaction medium contains more than 10% 4-carboxybenzaldehyde based on total reaction medium.

16. The method of claim 1 wherein the amount of the aromatic aldehyde after reaction is less than 60% of the amount of the aromatic aldehyde before reaction.

17. The method of claim 1 wherein the amount of the aromatic aldehyde after reaction is less than 1% of the amount of the aromatic aldehyde before reaction.

18. A method of reducing the amount of 4-carboxybenzaldehyde in a composition comprising:
reacting the 4-carboxybenzaldehyde in the presence of a reaction medium comprising an ionic liquid and a carboxylic acid, the reaction taking place in the absence of a hydrogenating agent and an oxidizing agent, to form terephthalic acid, 4-hydroxymethylbenzoic acid, or both;
recovering the terephthalic acid; and
isolating the 4-hydroxymethylbenzoic acid.

19. The method of claim 18 further comprising adding solid terephthalic acid containing solid 4-carboxybenzaldehyde to the reaction medium before reacting the 4-carboxybenzaldehyde, or introducing a solution containing the 4-carboxybenzaldehyde to the reaction medium before reacting the 4-carboxybenzaldehyde.

20. A method of decreasing the amount of a benzaldehyde in a composition comprising:
reacting the benzaldehyde in the presence of a reaction medium comprising a nucleophilic solvent, an ionic liquid, or combinations thereof, and a carboxylic acid, the reaction taking place at a pH in a range of 1 to 5 in the absence of a hydrogenating agent and an oxidizing agent, to form an aromatic carboxylic acid, an aromatic alcohol or both.

* * * * *